(12) United States Patent
Benner

(10) Patent No.: US 11,244,029 B1
(45) Date of Patent: Feb. 8, 2022

(54) HEALTHCARE MANAGEMENT SYSTEM AND METHOD

(71) Applicant: RXANTE, INC., Portland, ME (US)

(72) Inventor: Joshua S. Benner, McLean, VA (US)

(73) Assignee: RXANTE, INC., Portland, ME (US)

( * ) Notice: Subject to any disclaimer, the term of this patent is extended or adjusted under 35 U.S.C. 154(b) by 369 days.

(21) Appl. No.: 13/729,817

(22) Filed: Dec. 28, 2012

Related U.S. Application Data

(60) Provisional application No. 61/581,760, filed on Dec. 30, 2011.

(51) Int. Cl.
*G16H 20/10* (2018.01)
*G06F 19/00* (2018.01)

(52) U.S. Cl.
CPC ................ *G06F 19/3456* (2013.01)

(58) Field of Classification Search
CPC ........ G06Q 10/00; G06Q 50/22; G06Q 50/24; G06F 19/3456
USPC ........................................................ 705/2–4
See application file for complete search history.

(56) References Cited

U.S. PATENT DOCUMENTS

| | | | |
|---|---|---|---|
| 6,587,829 B1 * | 7/2003 | Camarda et al. | 705/3 |
| 6,802,810 B2 | 10/2004 | Ciarniello et al. | |
| 7,072,841 B1 * | 7/2006 | Pednault | G06Q 40/00 705/4 |
| 8,038,613 B2 * | 10/2011 | Stupp | G06F 17/18 600/300 |
| 8,214,224 B2 | 7/2012 | Rao et al. | |
| 8,543,422 B2 | 9/2013 | Maman et al. | |
| 8,595,167 B1 * | 11/2013 | Grieve | 706/45 |
| 8,666,926 B1 * | 3/2014 | Nease et al. | 706/50 |
| 2003/0212579 A1 | 11/2003 | Brown et al. | |
| 2005/0165626 A1 * | 7/2005 | Karpf | 705/3 |
| 2006/0241969 A1 * | 10/2006 | Wilhide | G06F 19/328 705/2 |

(Continued)

OTHER PUBLICATIONS http://www.adherishealth.com/, (retrieved on Jun. 11, 2015).

(Continued)

*Primary Examiner* — Mark Holcomb
(74) *Attorney, Agent, or Firm* — Nixon & Vanderhye, PC

(57) ABSTRACT

The disclosed methods and systems are generally directed to the combined application of predictive analytics with clinical decision analysis to provide optimal recommendations for the implementation of various health care management programs including, for example, prescription medication adherence interventions, and providing recommendations for medication adherence interventions for individual patients, based on predictions of patient adherence and predicted or expected responses to available interventions. Such interventions may be instituted in advance of a potential negative outcome, e.g., non-adherence, to prevent or reduce the occurrence of a negative outcome and realize greater return on investment. The disclosed systems and methods generally determine a predictive function based at least on historical patient data and predictive variables derived from the historical data, apply the predictive function to data of candidate patients and provide a recommended course of health care management based on an output of the predictive function applied to a clinical decision analysis.

34 Claims, 5 Drawing Sheets

(56) References Cited

U.S. PATENT DOCUMENTS

| | | | |
|---|---|---|---|
| 2008/0004904 A1* | 1/2008 | Tran | A61B 5/0006 705/2 |
| 2008/0201174 A1* | 8/2008 | Ramasubramanian et al. | 705/3 |
| 2008/0228525 A1 | 9/2008 | Weickert et al. | |
| 2010/0082367 A1 | 4/2010 | Hains et al. | |
| 2010/0205008 A1* | 8/2010 | Hua et al. | 705/3 |
| 2010/0228567 A1 | 9/2010 | Wulf | |
| 2014/0316797 A1 | 10/2014 | Biernacki et al. | |

OTHER PUBLICATIONS http://pharmaceuticalcommerce.com/information_technology?articleid=27195 (retrieved on Jun. 12, 2015).

http://www.cvshealth.com/our-businesses/pharmacy-advisor (retrieved Jun. 11, 2015).

http://www.cvshealth.com/sites/default/files/INSIGHTS%20ADHERENCE%202014.pdf (retrieved on Jun. 11, 2015).

http://www.fico.com/en/products/fico-medication-adherence-score (retrieved on Jun. 11, 2015).

https://www.optum.com/content/dam/optum/Landing%20Page/Medication%20Adherence%20Webinar%200613/Medication-Adherence-White-Paper.pdf (retrieved on Jun. 12, 2015).

\* cited by examiner

HEALTHCARE MANAGEMENT SYSTEM AND METHOD

TECHNICAL FIELD

The disclosure relates generally to the field of health care management, and more particularly to the combined application of predictive analytics with clinical decision analysis to provide optimal recommendations for the implementation of various health care management programs including, for example, prescription medication adherence interventions, and providing recommendations for medication adherence interventions for individual patients, based on predictions of patient adherence and predicted or expected responses to available interventions. Such interventions may be instituted in advance of a potential negative outcome, e.g., non-adherence, to prevent the occurrence of a negative health outcome and realize greater return on investment in such interventions.

BACKGROUND

In most known health care management systems, actual care being received by a patient is compared to established standards or methods for providing such care to determine if there is a variance between the care being administered and established standards of clinical excellence. When such a variance is identified, such known systems may identify a medically mismanaged patient and suggest pertinent medical care considerations to improve the care of patients that such a system may identify as being medically mismanaged. An inherent shortcoming of such an approach is that it is necessarily retrospective or reactive in nature, as opposed to being predictive. Because of the retrospective, or after the fact, nature of these approaches, these approaches are also fundamentally inefficient, both from a cost and patient well-being perspective. In other words, only after mismanagement occurs and is detected, and thus only after the expenditure of economic resources and potentially preventable risks to the patient are realized, are alternative therapies suggested or implemented. Moreover, many adverse health behaviors or outcomes are difficult or impossible to reverse with reactive interventions. One such example area that suffers from the types of problems associated with the reactive approach is prescription medication adherence.

With respect to the medication adherence example, only about 50% of people take prescription medications exactly as prescribed. Because many of those who stop taking their medications typically do so for what they perceive to be good reasons, the problem of medication non-adherence is more effectively prevented than treated after the fact. For many chronic therapies, premature discontinuation of certain medications results in preventable complications, and even death. Not only does medication adherence failure have an adverse impact on the patient, it has an enormous economic impact on society. It has been estimated that the cost to society of medication adherence failure is about $290 billion per year in direct and indirect costs. Because of this heavy burden on society, dozens of medication adherence interventions and programs have been proposed and implemented in an effort to improve medication adherence among certain patient populations. Some of these solutions include electronic monitoring, reminders to take medicines daily or to refill medications in a timely manner, patient education in the form of education materials and counseling, social support programs, economic incentives and rewards, and even directly observed therapy.

Medication adherence programs are also a lucrative business for organizations that provide them because the costs are typically borne by the pharmaceutical industry. Ongoing reforms to the U.S. health care system are bringing more attention to the problems associated with retrospective, or after the fact, care management, including medication adherence. For example, new quality of care measures have been developed to evaluate health care providers, such as, for example, doctors, hospitals and pharmacists, based on adherence to chronic medications among their patients. Health care payers, e.g., Medicare, Medicaid, private health plans and employers, are becoming increasingly attentive to medication adherence, especially for medications that can prevent or reduce hospitalization, surgery, disability and other high-cost medical events.

Many known effective medication adherence interventions are costly, and typically involve a combination of patient education, counseling by trusted health care professionals and persistent monitoring to address potential drug therapy problems as they occur. It is also the case that medication adherence programs are typically more effective in patients new to a therapy than those who have already discontinued therapy, making the need for prospective (as opposed to retrospective) management and intervention more imperative. Because about half of patients will be adherent without assistance or any intervention, the value of targeting adherence programs to the individuals who will benefit most is very high, especially in view of the high cost of such interventions. Moreover, because, as noted above, medication adherence programs are more effective at preventing non-adherence than convincing patients to re-start a discontinued medication, it would be advantageous to provide a medication adherence intervention solution that is predictive in nature as opposed to known systems that are typically reactive in nature.

To that end, approaches to predicting adherence have been attempted. These approaches differ fundamentally based on the source data being used to make the prediction. For example, these approaches include electronic databases containing a patient's past use of health care services, e.g., administrative claims for payments by doctors, hospitals and pharmacies; patient surveys; and electronic databases containing purchasing, credit and other consumer behavior linked to a patient's name and address. However, these proposed generic solutions suffer from a number of shortcomings and are not, by themselves, effective as predictors that are useful for providing cost effective, patient-specific medication adherence intervention. Moreover, these purported predictors are not coupled with any clinical decision analysis or determinations that compare the expected costs and effects of available interventions based on prediction outcomes, and thus cannot provide practical cost-effective tailored patient-specific intervention recommendations in advance that may greatly improve the chances of success of the intervention program.

BRIEF SUMMARY

What is needed is a care management program that combines predictive analytics with clinical decision analysis to provide tailored patient-specific intervention recommendations in advance of a negative behavior or outcome. This approach provides a cost-effective predictive tool that improves care management from both a cost and patient well-being perspective. To that end, the application discloses a system and method that combines predictive analytics with clinical decision analysis and ongoing effectiveness monitoring to provide patient-specific health care intervention recommendations in advance, e.g., before the occurrence of a potentially negative behavior or result, in an effort to avoid or prevent the potentially negative behavior or result from occurring in the first place.

In the medication adherence example, predictive analytics may be used to predict a patient-specific adherence level or score. The predicted adherence level or score may then be applied in a clinical decision analysis to provide a tailored patient-specific medication adherence intervention program in advance of potential non-adherence. In this manner, the disclosed system and method are useful to predict future medical behaviors (e.g., medication adherence) at the individual patient level, and to recommend an effective and tailored patient-specific intervention in advance that, if followed, will result in a better outcome. To provide even more robust and effective health care management, continued observation or tracking of patient medication use, for example, through the use of pharmacy refill data, or the like, may be recursively integrated with the disclosed systems and methods to provide improved ongoing patient management by continuously revising predictions and intervention recommendations based on the integration of such tracking information. Another example of the use of tracking data may include revising expected effects of interventions based on automated monitoring of populations receiving interventions.

Tracking provides many additional benefits not previously recognized. For example, some elements of the data used for prediction and decision analysis do not change over time, such as, for example, patient name, date of birth, etc. Other elements of the data used for prediction and decision analysis are time-varying, i.e., change over time. Examples of changing elements include how much experience the customer/patient has with the medication of interest, concomitant medications and conditions, health status, interventions received, etc. Tracking enables routine augmentation of the time-varying data on each patient (in batches and/or in real-time). This continued refreshing or augmentation of the data enables tracking of patient characteristics, adherence to the drug(s) of interest, variables needed to make predictions, and intervention performance. One key variable that may be tracked is the intervention performance in subgroups of patients to learn which patients respond best to each intervention. In this manner, the system may improve its predictive accuracy and intervention recommendations over time.

In general, historical patient data is analyzed in view of a dependent variable, e.g., the measure to be predicted, to define and extract certain independent predictive and indicator values that are subsequently used to generate a resultant data file. It will be understood that different and multiple sources of data may be used to determine any number of independent variables for use in developing the predictive function described below. The resultant data file is analyzed using one or more statistical methods to develop an optimized or best-fit predictive function when tested and validated against the historical patient data in view of the fact that actual future adherence can be determined with respect to the historical patient data. This predictive function is then applied to data of candidates for intervention to achieve a predictive score associated with each candidate patient. This predictive score is then supplied to a clinical decision analysis program that maps the predictive score to an optimal intervention, among a set of pre-defined interventions, based on the predictive score and other measures that may be applied by the clinical decision analysis. Rules for deploying interventions may be arbitrary and based on intuition or simple mapping algorithms. Clinical decision analysis, on the other hand, is a more quantitative approach to making decisions about the clinical care of individual patients. Decision analysis involves first identifying a decision to be made and the available courses of action. Next, the costs and benefits of each option may be estimated based on the best available evidence. Results from a diagnostic test or other predictive analysis may, for example, be one input when estimating costs and benefits for an individual patient. The optimal choice may then be calculated based on the decision maker's goal, such as, for example, and without limitation, minimizing cost, maximizing benefits, maximizing the benefits gained under a specific budget, or the like. According to certain example aspects of the disclosure, is the use of predictions and observed intervention effects from tracking data (and even other data and information) to inform the decision. The result is a recommended intervention based on the combination of predictive analytics (e.g., the score) and the application of clinical decision analysis. It will be appreciated that the set of pre-defined interventions may include no intervention at all. As noted above, a significant number of candidates will take medications as prescribed and will not require any further reminders or intervention to continue taking the medication. By including no action among the set of pre-defined recommendations, and mapping patients with appropriate predictive scores to no intervention based on a decision analysis, the system and method described herein realizes further cost effectiveness by concentrating resources on potentially non-adherent candidates and not unnecessarily expending resources on candidates who do not require intervention.

The process of prediction followed by program recommendation may be repeated in a recursive manner at any desired interval (e.g., monthly or weekly), to facilitate ongoing tracking and management of adherence and for providing improved results by continuously revising predictions and intervention recommendations based on the integration of tracking information. The iterative nature of the tracking process provides many important benefits, such as, for example, allowing new starters of the drug of interest to "enter" the management process soon after beginning therapy—when interventions are most likely to be effective. Another benefit of integrating tracking information to revise predictions and intervention recommendations is using recent past information to inform new predictions and recommendations by making the system's predictions more accurate over time, and providing additional precision to initial predictions that may have been less precise. Moreover, by tracking performance of deployed interventions over time, the system may generate more precise inputs for the clinical decision analysis, and thus provide more effective recommendations.

In one example embodiment, a method for predicting medication adherence and recommending a patient-specific medication adherence intervention is provided. According to this example, the method includes: receiving data including historical patient data sufficient to determine actual adherence to a given medication of interest, developing a predictive function based on the historical data, applying the predictive function to patient data of candidates for medication adherence intervention to obtain an adherence score, and using the adherence score in a clinical decision analysis that provides a recommended intervention based on the adherence score and other variables. The process of developing a predictive function based on the historical data, may include, among other things: defining relevant time periods for analyzing the historical data; defining a dependent variable indicative of a measure to be predicted; defining at least one independent predictor variable based on at least one of an attribute of the patient, an attribute of a drug regimen and/or an attribute of a health care system based on the historical patient data from the defined time periods; creating a resultant data file including the dependent and independent variables; and deriving a prediction function based on the resultant data based on a comparison of multiple statistical methods (e.g., ensemble methods). The predictive function is then applied to data of candidates for predictive medication adherence intervention to produce an adherence score for each candidate. This adherence score is then used in a clinical decision analysis which may, for example, be implemented in the form of an intervention recommendation matrix that maps the adherence scores to recommend interventions to determine an optimal recommended medication intervention from among the pre-defined group of potential interventions based at least in part on the adherence score. In addition to the adherence score, the clinical decision analysis may include other inputs, including, for example, the true positive, true negative, false positive and false negative rates for the predictive function, cost per patient of each defined intervention program, effectiveness (e.g., incremental probability of being adherent, and marginal gain typically in dollars), to provide further granularity to the decision analysis based on an output of the prediction engine. Inputs to the clinical decision analysis may be specific to a given candidate, or others like or similar to the candidate.

Additionally, the method may incorporate a recursive or iterative tracking process that incorporates recent past information of current candidates to generate a revised prediction based on current results. In other words, the process of prediction followed by program recommendation may be repeated in a recursive manner at any desired interval (e.g., monthly or weekly), to facilitate ongoing tracking and management of adherence and for providing improved results by continuously revising predictions and intervention recommendations based on the integration of such tracking information.

In another example embodiment, a system is provided that includes a prediction engine that provides predictive analytics coupled with an intervention recommendation engine that performs clinical decision analysis.

The prediction engine includes, for example, a computer programmed to process data which may be in the form of a database. The prediction engine is provided with, for example, historical patient data, from which actual adherence may be calculated. The prediction engine may then be used to develop a predictive model calibrated to the patients and the target drug of interest. In this connection, a number of time periods, dependent variables (e.g., the measure to be predicted) and independent variables (e.g., predictors) are defined. Applying these variables and periods to the historical patient data, a resultant data file is generated. The resultant data file is subjected to statistical processes, for example, ensemble methods, that use multiple statistical methods for analysis on the resultant data file to generate a prediction model or function that provides a best fit to the historical, or known, patient data. Patients that are candidates for the medication adherence program are identified, and for each batch of identified candidates, available historical medical data, preferably in electronic form, including, for example, prior pharmacy claims, medical claims, and/or electronic medical records, may be provided. This data is stripped of patient identifiers and other data to comply with privacy regulations. This data file is then converted into a patient-level file that includes the variables identified and derived during the process described above. The prediction model or function is then applied to the patient-level file and outputs a predictive adherence score for each patient.

Clinical decision analysis based on the output of the prediction engine is then accomplished by an intervention recommendation engine. The intervention engine is a computer based application that receives various inputs, including the predictive adherence score, and provides a patient-specific recommended intervention tailored to each patient in the candidate batch. The intervention engine may receive various additional inputs, such as, for example, and without limitation, the true positive rate, true negative rate, false positive rate and false negative rate of the prediction engine, adherence goals for the patient or population, cost per patient for each defined adherence program, effectiveness (e.g., incremental probability of being adherent) in patients like the one being screened (e.g., candidate specific), and marginal gain (typically in dollars) for each incremental unit of effectiveness, etc. Each adherence score received from the prediction engine is then input into a computer implemented decision analysis matrix, along with other information about the patient and available interventions, to determine the optimal intervention among a pre-defined group of potential interventions. In this regard, an optimal intervention among the pre-defined group of potential interventions to be recommended may be chosen based on any number of factors and goals determined by the operator, such as, for example, maximized expected value of the overall adherence intervention strategy or return on investment.

The results of applying the intervention engine to the output of the prediction engine may be provided in a report that identifies the adherence score (e.g. prediction) and intervention recommendation for each candidate patient based on the adherence score and other variables input into the intervention engine. Reports may be revised weekly, monthly, or on any desired interval to take advantage of recent data in making new or revised predictions and recommendations on the same patients, and include new users of the drug of interest in the management system. For example, the system may incorporate a recursive or iterative tracking process that incorporates recent past information of current candidates and effects of available interventions to generate revised predictions and recommendations based on current results. In other words, the process of prediction followed by program recommendation may be repeated in a recursive manner at any desired interval (e.g., monthly or weekly), to facilitate ongoing tracking and management of adherence and for providing improved results by continuously revising predictions and intervention recommendations based on the integration of such tracking information.

An example of implementation of such a system is provided for illustrative purposes herein. For example, an implementation entity or program sponsor, e.g., drug company, employer or whomever is paying for the adherence program, identifies potential candidate patients and potential interventions. In this example, a health insurer or drug company may identify new users of a cholesterol medication (e.g., a "statin" drug) as candidates and specify three types of interventions, e.g., refill reminders, telephone calls or live physician office counseling. The implementation entity or program sponsor provides historical patient data about patients who would have been candidates for the adherence program in the past. The prediction engine, as outlined above, determines a predictive function. This function is applied to candidate patient data and outputs an adherence score for each patient. For example, patient no. 100, a 26 year old woman who started a statin today, has a 1-year statin adherence score of 58 (e.g., 58% chance of being adherent). The intervention engine then takes this information from the prediction engine and by mapping or applying the clinical decision analysis to the adherence score, determines that a parameter used as defining what is optimal, e.g., return on investment, is highest when women aged 75-85 with a statin adherence score in the range of 40-64 receive telephone counseling. Other rules in the intervention engine are applied, including, for example, the number of telephone counseling sessions available for distribution this month, whether the patient has a telephone number on file, whether the patient speaks English, expected outcomes if patient 100 receives a call versus any of the other options, etc. The patient-specific intervention recommendation output by the system is that patient no. 100 should receive telephone counseling. In a similar manner, for all patients in the patient-level file, a score and recommended intervention (including "no intervention" for some patients) are provided. Of particular importance to the application is that the system is predictive in nature and that the recommended interventions may be provided before any negative behavior is engaged in, thus acting to potentially prevent the negative behavior from occurring and realizing significant savings in both cost (to the individual and society) and increased patient well-being. Another important feature is that predictions and recommendations can be refreshed on desired intervals to incorporate tracking or accumulating data on each patient or intervention, and thereby improve the accuracy of predictions.

Of course, it will be understood that the disclosure is not limited to medication adherence, and that similar predictive analytics in combination with clinical decision analysis can be brought to bear on any number of conceivable health care management protocols, including, for example, to predict hospital readmissions, emergency room visits, surgical complications, or other events that a health system or health plan might wish to prevent with a health care management improvement program. For example, the disclosed systems and methods may be used to effectively and efficiently lower a rate of hospital readmissions within 30 days following discharge for patients who experienced a myocardial infarction (i.e., a heart attack). In this example case, the hospital could provide a range of follow-up services, such as a medication reconciliation by a pharmacist at the time of discharge, telephonic counseling by a nurse, or home visits from a case manager to review diet, exercise, and/or medication recommendations. Data from the electronic medical records system of the hospital may be used to create the predictions of each patient's risk of readmission within 30 days, and information on the cost and effectiveness of each available intervention could be used to conduct the clinical decision analysis. In this example case, the decision analysis may seek to improve the cost-effectiveness of post-discharge follow-up, or reduce the cost per readmission avoided. The result would be a recommended follow-up intervention (or recommendation of no intervention) for each individual patient.

It will also be understood that any number of conceivable parameters may be used to determine what might be considered to be an optimal recommended intervention or health care management protocol. One example of a parameter that may be used to determine what might be considered optimal may be economic in nature, such as, for example, return on investment or a cost-effectiveness ratio. While examples discussed herein may relate to return on investment, it will be understood that return on investment is but one of any number of conceivable parameters that may be used, and that return on investment as discussed herein is intended to be illustrative, not limiting.

BRIEF DESCRIPTION OF THE DRAWINGS

Exemplary embodiments will be better understood and appreciated in conjunction with the following detailed description of example embodiments taken together with the accompanying drawings in which like reference numerals refer to like elements, and wherein.

DETAILED DESCRIPTION

A detailed description of a care management system and method that combines predictive analytics with clinical decision analysis to provide tailored patient-specific recommendations for managing a set of health care programs aimed at preventing a negative behavior or outcome is provided. The example system and method described herein provides recommendations in an effort to avoid or prevent the potentially negative behavior or outcome from occurring or to improve the chances of a good outcome. An example embodiment will be described herein with respect to medication adherence in which predictive analytics may be used to predict a patient-specific adherence score or level. The predicted adherence score or level may then be applied in an automated clinical decision analysis to provide or recommend a tailored, patient-specific medication adherence intervention program in advance of potential non-adherence. In this manner, the disclosed system and method are useful to predict future health care behaviors (e.g., medication adherence) at the individual patient level, and to recommend effective and tailored patient-specific intervention recommendations in advance which, if followed, will efficiently improve the chances of the desired health behavior.

While the following description is provided with respect to a medication adherence example, it will be understood that the disclosure is not so limited, and that similar predictive analytics in combination with clinical decision analysis can be brought to bear on any number of conceivable health care management protocols, including, for example and without limitation, to predict hospital readmissions, emergency room visits, surgical complications, or other events that a health system or health plan might wish to prevent with a health care management program.

Figure 5:
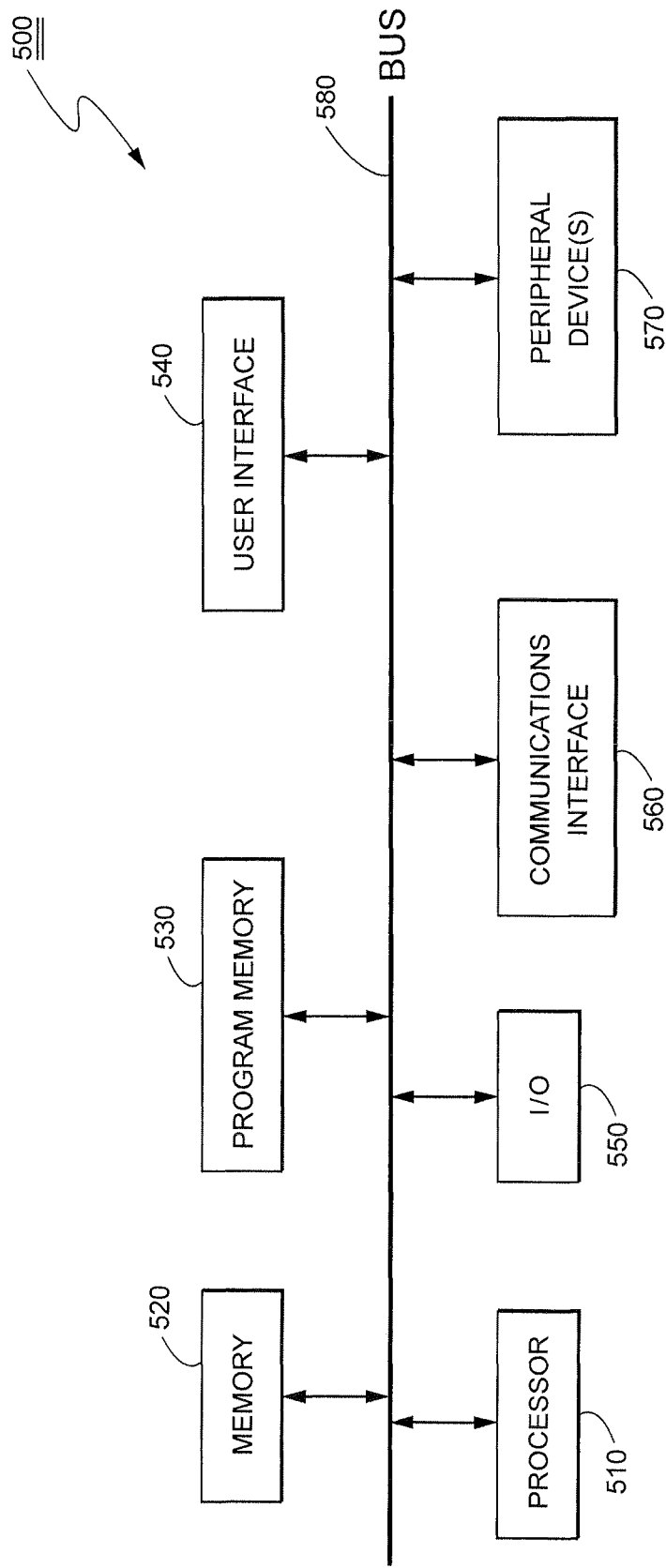
FIG. 5 is an illustrative schematic block diagram of elements of a computing system that may be used to perform functions associated with an example embodiment.

In the example described herein, data may be input, manipulated and analyzed using a specially programmed computer system. This computer system may also be used to process data to derive a prediction function, and to analyze outputs of the application of the prediction function to candidate patient data to provide a recommended course of action, e.g., a medication adherence intervention program in this example. An illustrative schematic block diagram of elements of a computing system that may be used to perform functions associated with an example embodiment will be discussed with respect to FIG. 5, which illustrates the basic requirements of such a computer system 500. In FIG. 5, a bus 580 interconnects a processor 510 with various hardware, firmware and software elements including, for example a memory 520 which may be used to store historical and candidate patient data as well as patient-specific patient-level data generated by the example health care management system described herein. Moreover, it will be understood that this memory is not necessarily integrated with the computing system 500, but may be operatively coupled to the system in any manner, including, for example, via a secured cloud, dedicated links, the Internet, or the like. The computer system 500 may also include a program memory 530 containing various instructions or application software that may be used to operate the processor 510 and to process data, including, for example, machine-level code to run the basic operations of the processor as well as software for implementing the illustrated health care management system. It will be noted that the program memory 530 may also be integrated in whole or in part with the processor 510 and is not necessarily a separate element as shown in the drawings. The computer system 500 may further include several interfaces that enable various interactions with the system 500. For example, a user interface 540 is provided that allows operators to program the system 500 as well as to enter and manipulate data, and to extract information that may be stored in the memory 520 or other databases connected to the system 500. The user interface 540 may be, for example, in the form of a display and associated input/output devices, such as, for example, a keyboard, mouse, gesture pad, or the like (not shown). The system 500 may also include a communications interface 560 that provides connections for allowing the system 500 to receive and transmit information to and from external sources via various communications links, including, for example, the Internet, an electronic health records system, dedicated links, secure clouds, or the like. For example, the communications interface 560 may be used to receive historical patient data and candidate patient data or patient-level files generated at another system or site. It is also contemplated that the system 500 may include peripheral devices 570, such as, for example, external memory, a printer, etc. While an example general computing system 500 has been described herein, it will be appreciated that those skilled in the art would be able to devise any suitable computing system to achieve the objects and features described herein with respect to the disclosed example health care management system.

Figure 1:
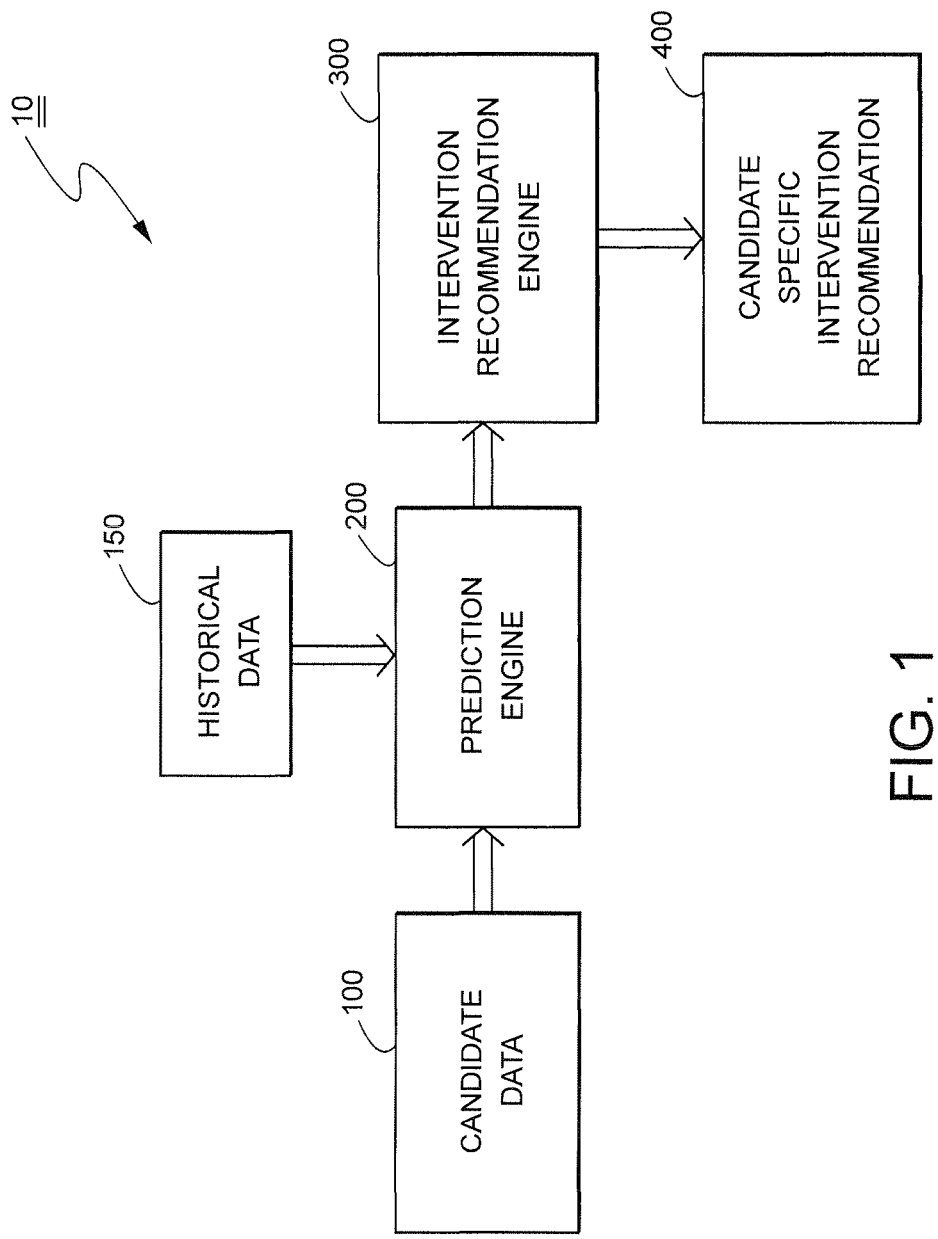
FIG. 1 is an illustrative block diagram of an example embodiment.

Turning to FIG. 1, an illustrative block diagram showing elements of an example embodiment is provided. The basic elements 10 are described very generally with respect to FIG. 1 and will be described in further detail below with respect to the remaining drawings. The system includes, for example, candidate patient data 100, which is processed as described herein and provided to a prediction engine 200. The prediction engine 200 is developed as described below and includes development of a prediction function which is based, at least in part, on an analysis of historical patient data 150 which may include historical data on intervention performance (for example, and without limitation, tracking data). When the prediction function of the prediction engine 200 is applied to the candidate patient data 100, a tailored patient-specific score is output and provided to an intervention recommendation engine 300 that performs automated clinical decision analysis based on the patient-specific score output by the prediction engine 200 and historical data on intervention performance, which may be included as part of the historical patient data 150. The intervention recommendation engine 300 provides a patient specific intervention recommendation 400 for each patient in the candidate patient pool for whom a predictive score is provided by the prediction engine 200.

An example embodiment directed to medication adherence is described herein. In the medication adherence example, predictive analytics may be used to predict a patient-specific adherence level or score for each candidate in a batch of candidate patients for medication adherence intervention. The predicted adherence level or score may then be applied in a clinical decision analysis with other attributes of the patient and attributes of the available interventions to provide a tailored patient-specific medication adherence intervention program to improve medication adherence. In this manner, the disclosed system and method are useful to predict future medical behaviors (e.g., medication adherence) at the individual patient level, and to recommend an effective and tailored patient-specific intervention in advance that, if followed, will improve the chances of the desired health behavior and outcomes.

A general overview of an example system and method, with respect to a medication adherence example, is disclosed herein. It will be understood that products that may be a target of medication adherence programs may vary and include, for example, individual drugs and other medical products, classes of drugs or combinations of products. At the outset, a set of potential interventions that may be available to the candidate patients may be predetermined or pre-defined by the program sponsor, e.g., whoever is paying for the adherence programs, such as, for example, a health insurer, drug company or employer, and the implementation entity, e.g., whoever is deploying the adherence program, such as, for example, a care management firm, a physician network, a pharmacy chain, etc. It will be understood that the implementation entity and the program sponsor may be the same organization, such as in the case of a pharmaceutical company, a pharmacy benefits manager, health plan, or the like. The identification of candidate patients 100 may be done by the implementation entity who may apply rules agreed upon with the program sponsor, as an example. Alternatively, the system operator or administrator may identify candidate patients if the implementation entity provides access to the necessary patient data.

For example, a protocol sponsored by a health insurer might call for the implementation entity to identify patients new to a specific medication or drug based on filled prescriptions for the drug, preceded by one year without any fills for the drug of interest. Individuals meeting these and/or other inclusion criteria may be candidates for medication adherence intervention, which may be pre-defined, for example, as being in the form of: mailed refill reminder letters, counseling calls from the pharmacy welcoming them to the new drug therapy, or a dedicated live counseling session with a nurse at the patient's doctor's office.

Figure 2:
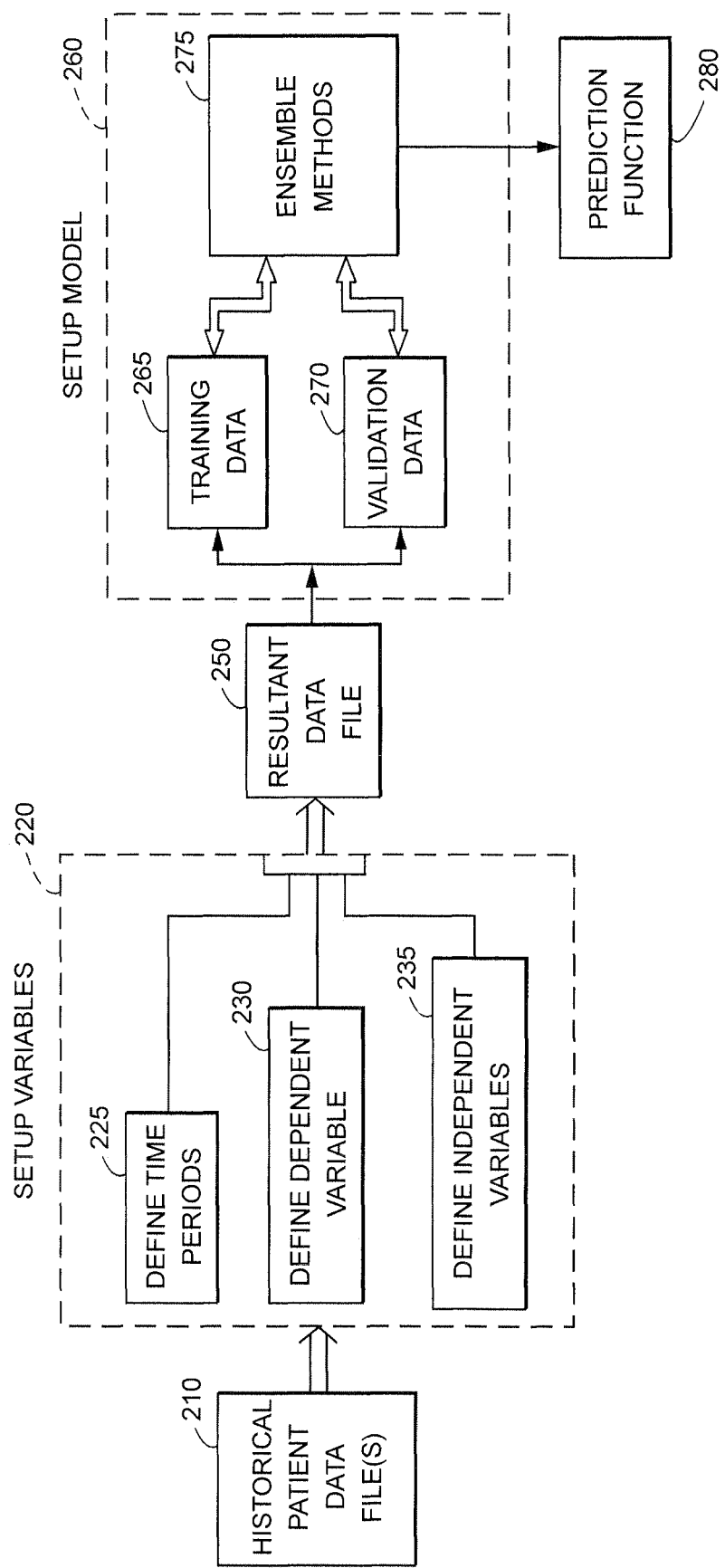
FIG. 2 is an illustrative block diagram of an example setup procedure used to define a prediction function in accordance with an example embodiment.

As a first step in this illustrative example, a prediction function, which may be typically unique to each drug or class of drugs, may be created using a setup procedure, which is illustrated generally in FIG. 2. As illustrated in FIG. 2, historical patient data 210, which may be in the form of a retrospective data file (or multiple files) from the implementation entity or program sponsor, is provided. Data in these files may include, for example, demographic, survey, clinical and/or administrative claims data about patients who would have been candidates for the adherence program, plus filled prescriptions data to allow for calculation of actual adherence after initiation of the medication therapy of interest. It will be understood that the data sources may vary and may include other example data, such as, for example, administrative claims, electronic medical records, lab results, patient surveys, sociodemographic detail, consumer purchasing data, etc. It will also be understood that different and multiple sources of data may be used to determine any number of independent variables for use in developing the predictive function described below.

The historical patient data 210 is analyzed and used during setup 220 to define certain variables 225, 230 and 235, for example, which may be used to determine a prediction function 280. For example, certain time periods 225 may be defined to assist in the extraction of various variables. Time periods of interest 225 may include, for example, an inception window or range of dates between filled prescriptions for the target medication which may be used to identify candidate patients for the adherence program. An index date for each patient which reflects the date of the first filled prescription for the target medication during the inception window may also be defined. It may also be useful to define a look back period during with the pre-index information is collected about each patient. A common example look back period is one year, but it will be understood that the look back period can range from zero days to many years. In addition, a follow-up period may be defined. A common follow-up period may typically be one year, but the follow-up period may range from one day to many years.

It is next preferable to define a dependent variable 230, sometimes also referred to as the measure to be predicted. In the medication adherence example, a common measure of medication adherence is the binary outcome of a proportion of days covered being greater than or equal to eighty percent. In other words, this dependent variable 230 would be satisfied if the patient obtained sufficient prescriptions to have the medication on hand for at least eighty percent of the days in the follow-up period. It will be understood that definitions of adherence may vary and that the definition set forth above made by way of illustrative non-limiting example. Other examples may include, proportion of days covered, medication possession ratio, discontinuation, etc. Additionally, threshold values may likewise vary, e.g., >=80%; >=70%; >=60%, etc. With the dependent variable 230 defined, it may then be useful to define a number of independent variables 235.

Independent variables 235, may be developed based on published studies of factors associated with adherence in a particular therapy area. These may, for example, fall into three broad category areas. One broad category area may be, for example, attributes of the patient, e.g., age, sex, county of residence, health status and prior health care utilization. Another broad category may include, for example, attributes of the target drug regimen, e.g., specific drug, strength, quantity dispensed, cost, etc. A third broad category may include, for example, attributes of the health care system, e.g., prescriber's specialty, number of pharmacies used, health plan design, etc.

Independent variables 235 may include variables known to be predictive of adherence and may include variables not known to be associated with adherence, but which can be rapidly tested using data mining methods to derive these from the patient data itself. For example, software running on the computer system 500 may be used to automatically create independent variables. These variables generally may relate to the presence/absence and frequency of all possible drugs, diagnoses and procedures in the patient look-back period. Survey data may also be included in the provided data and all possible responses may also be included. It will be understood that different and multiple sources of data may be used to determine any number of independent variables for use in developing the predictive function.

A resultant data file 250 is generated to include the setup variables 220 that are generated as described above. Patient data files may be augmented and restructured to provide a common data structure for the resultant data file 250 in order to more efficiently process the data contained in the resultant data file 250. The resultant data file includes information for each patient of interest from the historical patient data files 210 and include the setup variables 220 discussed above.

Once the resultant data file 250 is created, it is provided to a further model setup procedure 260, that will result in a prediction function 280 that is then applied to candidate data to produce a patient-specific score, in this case an adherence score. Creation of the prediction function 280 is discussed in more detail herein. In general, the resultant data file is analyzed using multiple statistical methods to develop the best predictive function when tested and validated against the historical patient data in view of the fact that actual adherence can be determined with respect to the historical patient data. As a specific example, the resultant data file 250 may be divided into two parts, a "training" data file 265 and a "validation" data file 270. The system may then use, for example, multiple statistical methods 275, including, for example, any one or more of the following: logistic regression, random forests, classification and regression trees (CART), stacking, boosting, or the like, on the training data 265. These statistical methods may generally be combined, and as such, be referred to as ensemble methods 275 for determining or creating a model or predictive function based on the training data 265 that will yield highly predictive results. For example, as noted above, the resultant data file 250 may be partitioned into two parts, the "training" data 265 and the "validation" data 270 as described above. For the purposes of example, the resultant data may be randomly partitioned so that eighty percent (80%) are the "training" data 265 and the remaining twenty percent (20%) of the resultant data are in the "validation" data 270 set. It will be understood that any statistically proper partitioning may be selected based on the type of analysis and regression to be applied to the data. The models or predictive functions are developed and tested using the training data 265 over multiple statistical methods as discussed above (e.g., ensemble methods), and then testing the predictive function against the validation data 270, which is also commonly referred to as held-out data. A predictive function that is derived from the training data 265 may then be applied to the validation data 270, and the predictive function that is determined to perform best on the validation data 270 is selected as the predictive function to be applied to the candidate patient data as described below. It will be understood that any number of other possible statistical methods may be used to generate the resulting prediction function, and that the system and method disclosed is not limited to the particular example statistical methods described herein. In this manner, the independent variables or predictors are used to predict the dependent variable using the predictive function 280 created on the basis of the historical patient data 210.

Figure 3:
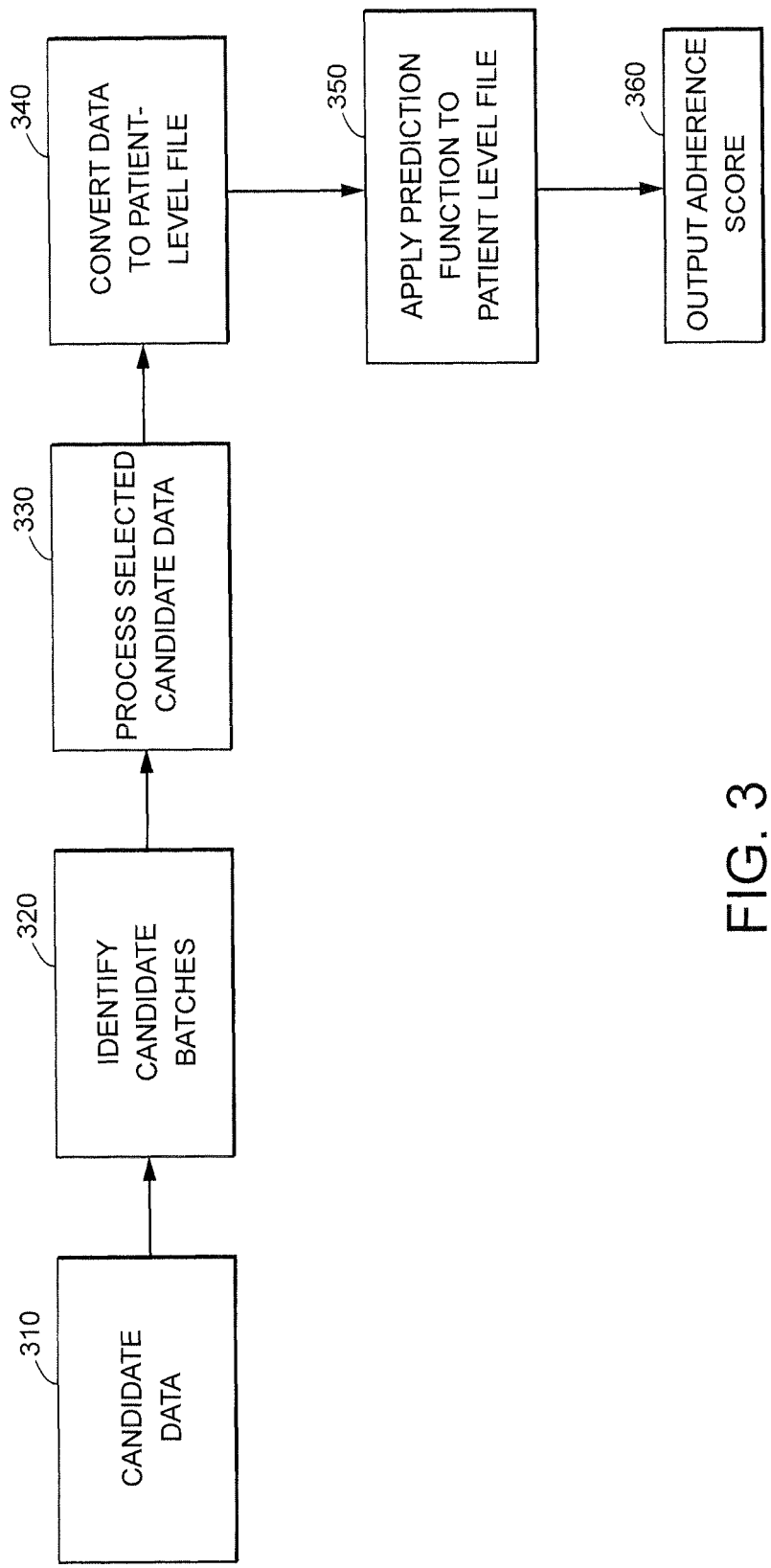
FIG. 3. is an illustrative block flow diagram describing an example embodiment with respect to implementation of a prediction function.

This predictive function is then applied to data of candidates for predictive intervention to achieve a predictive score associated with each candidate patient, as illustrated, for example, in FIG. 3. With reference to FIG. 3, the implementation entity provides candidate patient data 310 for application to the prediction function. This candidate patient data may be the same or similar to the candidate data 100 discussed above with reference to FIG. 1, and may grow with each iteration over time, such as, for example, as a result of incorporating tracking information as discussed herein. The candidate data 310 may be provided by the implementation entity who may, for example, screen patients who fill prescriptions for the therapy of interest, and then identifies patients who meet criteria to be candidates for the adherence program. Candidates may be accumulated into batches 320, for example, with respect to a defined period of time, e.g., daily, weekly, monthly, etc. For each batch of candidates 320 the implementation entity may provide available historical data from its electronic warehouse, and this historical data may include, for example, prior pharmacy claims, medical claims, electronic medical records, or the like. These data may then be processed 330 to be stripped of patient identifier information prior to sending to comply with applicable privacy regulations. The selected candidate data 330 is then converted into a patient-level analytical file 340 for each candidate in a given batch. The patient-level analytical file 340 includes the independent variables identified and defined during the setup phase described above. The prediction function 280 created during the setup process described above is applied 350 to the patient-level files 340 and outputs a predictive score, e.g., an adherence score 360 that is specific to each patient in the candidate batch 320, which reflects the probability of the patient experiencing the outcome represented by the dependent variable.

It is also contemplated that the disclosed system may also be applied in real-time, such as, for example, when triggered by an event for a specific patient, as distinguished from the batch mode operation described above. For example, and without limitation, in the setting of a health care organization using an electronic medical record with electronic prescribing capabilities, the system may be used to help doctors identify patients in need of adherence intervention immediately after writing a prescription. In this example, the system may be embedded in the electronic prescribing system, allowing the system to recognize a written prescription for a qualifying medication, fetch the patient's historical clinical data and apply the predictive function and clinical decision analysis. The system may then issue an intervention recommendation to the prescriber, as appropriate.

Another example of real-time application is in the setting of a pharmacy chain using, for example, a dispensing software system that also contains customer historical prescription data. In this example, the system may be embedded in the pharmacy dispensing system, allowing it to recognize a dispensed prescription for a qualifying medication. The system may then fetch the customer's historical medication utilization and/or other data, apply the predictive function and clinical decision analysis, and issue an intervention recommendation to the pharmacy personnel, as appropriate.

In yet another example of real-time delivery is the setting of a hospital or hospital system using an electronic database that contains clinical data from the patient's stay. According to this example, the system may be embedded in the hospital's electronic records system, allowing it to recognize when a patient is discharged from the hospital, fetch the patient's clinical information, apply the predictive function and clinical decision analysis, and recommend an intervention to prevent or at least reduce the likelihood of readmission.

Figure 4:
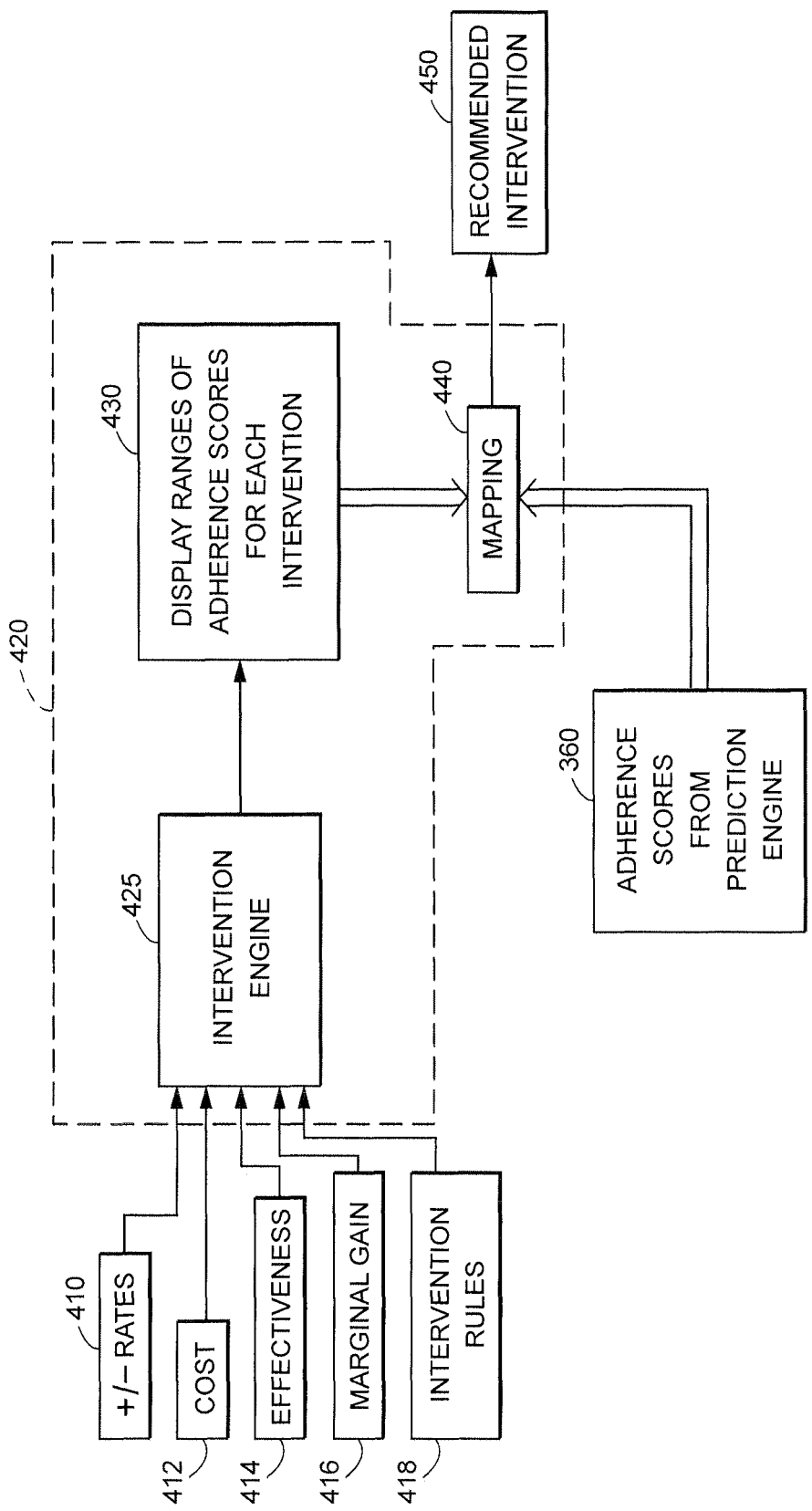
FIG. 4 is an illustrative block diagram of a clinical decision analysis according to an example embodiment.

The predictive adherence scores 360 are supplied to a clinical decision analysis program that maps the predictive score to an optimal intervention, among a set of pre-defined interventions, based on the predictive score and other measures that may be applied by the clinical decision analysis, as illustrated in FIG. 4. As set forth above, a goal of the system and method described herein is to recommend an optimal adherence program from among a set of pre-defined intervention programs, including, of course, recommending no program at all for those whose score indicates a patient that is highly likely to be adherent without intervention, and to tailor the recommendation for each individual candidate in a given batch. The system and method may be used to select patients for an individual adherence program, or to select an optimal intervention for a given patient from a set of discrete choices. The selection of an intervention for a given patient or adherence score relies on implementation of an automated clinical decision analysis, that, in addition to the predicted adherence score described above, takes into account other variables that help maximize expected value based on the program sponsor's criteria. These variables may include measures of the cost and effects of each available intervention, on average or as a function of patient characteristics.

For any given implementation the system and method described herein may additionally provide ongoing tracking and management services. The tracking and management services include re-application of the prediction engine and recommendation engine periodically. As a result, the tracking function may identify new candidates (e.g., patients who initiated the drug of interest) and may be used to revise the predictions and recommendations on previously screened candidates in light of additional data on patient medication use and response to intervention. This may be achieved by repeating the processes described with respect to FIGS. 3 and 4 on a timed interval, such as, for example, weekly or monthly or may be achieved in real-time. On second and subsequent iterations, the candidate data 310 provided by the implementation partner may also contain a mix of new and previously screened candidates. The prediction and recommendation engines are then applied to the new candidate data, and recommendations are reported for each candidate. Changes in recommended interventions for previously screened candidates may be reflected in a report of the adherence predictions and recommended interventions discussed below. Tracking enables routine augmentation of the time-varying data on each patient (in batches and/or in real-time). This continued refreshing or augmentation of the data enables tracking of patient characteristics, adherence to the drug(s) of interest, variables needed to make predictions, and intervention performance. One key variable that may be tracked is the intervention performance in subgroups of patients to learn which patients respond best to each intervention. In this manner, the system may improve its predictive accuracy and intervention recommendations over time.

Turning to FIG. 4, an intervention engine 420 is illustrated. To facilitate timely health care management interventions, it is preferable that the intervention engine 420 be automated, e.g., software based (of course, any suitable means for providing an intervention engine 420 may be used). The intervention engine 420 is set up by providing a number of inputs for optimization. As an example, return on investment may be the optimal outcome specified by the program sponsor. While the example illustrated herein uses return on investment as a measure of optimization, it will be understood that the clinical decision analysis may optimize other potential outcomes, such as, for example, population adherence rates, clinical outcomes, such as heart attacks prevented, or patient satisfaction. Alternatively, another example approach may be to match patients to interventions in a way that considers what risk factors the patient has for non-adherence when the prediction is made, for example, high copay for a drug results in recommended copay assistance.

However, for ease of understanding an example in which economic outcome, e.g., return on investment, is optimized is described. In that example case, additional inputs to the automated clinical decision analysis or intervention engine 420, may include, for example, true positive, true negative, false positive and false negative rates 410 of the prediction function. These rates are properties of the prediction function and the manner in which it was created. In other words, these inputs are characteristics of the model, such as, for example, empirically determined accuracy that is a function of statistical properties of the implementation. In addition, other inputs having relevance to return on investment, including, for example, cost per patient of the various interventions 412, expected effectiveness on adherence of each particular intervention in patients like the one being screened 414 (e.g., the increased chance of adherence as a percentage), and marginal gain 416 which can either be provided by the program sponsor or may be calculated. The intervention engine may also consider specific intervention rules 418 to guide intervention selection, such as, for example, capacity constraints and logic not to recommend telephone calls to patients who do not have a phone number available. These inputs may serve to stratify the data and are provided to the input side 425 of the automated clinical decision analysis 420. The clinical decision analysis engine 420 may also optionally display ranges of adherence scores or other patient profile information for which available interventions are computed to be optimal 430. The adherence scores 360 from the prediction function may then be automatically mapped 440 to the ranges displayed 430 to provide recommended interventions 450 for each patient from the set of pre-defined interventions based on the adherence scores 360 and other inputs 410, 412, 414, 416. The result is a recommended intervention 450 based on the combination of predictive analytics (e.g., the score) and clinical decision analysis based on multiple inputs, including the score (e.g., mapping). It will be appreciated that the set of pre-defined interventions may include no intervention at all. As noted above, a significant number of candidates will take medications as prescribed and will not require any further reminders or intervention to continue taking the medication. By including no action among the set of pre-defined recommendations, the system and method described herein realizes further cost effectiveness by concentrating resources on potentially non-adherent candidates and not unnecessarily expending resources on candidates who do not require intervention.

After the adherence scores 360 are mapped to the recommended interventions 450, a report of the adherence predictions 360 and recommended interventions 450 may be provided to the implementation entity and/or program sponsor in the form of and easy to use file, for example, a file with one row per patient and columns for patient ID, adherence score and recommended intervention.

An example of implementation of the example system discussed above is provided for illustrative purposes herein. For example, an implementation entity or program sponsor, e.g., health insurer, employer or whoever is paying for the adherence program, identifies potential candidate patients and potential interventions. In this example, a health insurer may identify new statin users as candidates and specify three types of interventions, e.g., refill reminders, telephone calls or live physician office counseling. The implementation entity or program sponsor provides historical patient data about patients who would have been candidates for the adherence program in the past. The prediction engine, as outlined above, determines a predictive function. This function is applied to candidate patient data and outputs an adherence score for each patient. For example, patient no. 100, a 76 year old woman who started a statin today, has a 1-year statin adherence score of 58 (e.g., 58% chance of being adherent). The intervention engine then takes this information from the prediction engine and by mapping the adherence score, determines that a parameter used as defining what is optimal, e.g., return on investment, is highest when women aged 75-85 with a statin adherence score in the range of 40-64 receive telephone counseling. Other rules in the intervention engine are applied, including, for example, checking the number of telephone counseling sessions available for distribution this month, whether the patient has a telephone number on file, whether the patient speaks English, the expected outcomes if patient 100 receives a call versus any other options, etc. If all necessary conditions are met, the patient-specific intervention recommendation output by the system is that patient no. 100 should receive telephone counseling. In a similar manner, for all patients in the patient-level file, a score and recommended intervention (including "no intervention") are provided. Of particular importance to the application is that the system is predictive in nature and that the recommended interventions are provided before any negative behavior is engaged in, thus acting to potentially prevent the negative behavior from occurring and realizing significant savings in both cost (to the individual and society) and increased patient well-being.

It will also be understood that the outcome that is predicted and/or managed by the health care management system and method described herein is not limited to the illustrative example of medication adherence. For example, the system and method may be used to predict hospital readmissions, emergency room visits, surgical complications or any other conceivable medical event that a health system or health plan may want to prevent with a care improvement program.

For example, the disclosed systems and methods may be used to effectively and efficiently lower a rate of hospital readmissions within 30 days following discharge for patients who experienced a myocardial infarction (i.e., a heart attack). In this example case, the hospital could provide a range of follow-up services, such as a medication reconciliation by a pharmacist at the time of discharge, telephonic counseling by a nurse, or home visits from a case manager to review diet, exercise, and/or medication recommendations. Data from the electronic medical records system of the hospital may be used to create the predictions of each patient's risk of readmission within 30 days, and information on the cost and effectiveness of each available intervention could be used to conduct the clinical decision analysis. In this example case, the decision analysis may seek to improve the cost-effectiveness of post-discharge follow-up, or reduce the cost per readmission avoided. The result would be a recommended follow-up intervention (or recommendation of no intervention) for each individual patient.

As another example, the disclosed systems and methods may be applied to prevent or reduce hip fractures in the elderly. In this example, a hospital or health insurer may seek to reduce the risk of hip fractures in ambulatory older patients because falls commonly lead to fractures of the hip, which can lead to costly and sometimes permanent disability. In this example, the dependent variable may be hip fracture, and the goal of the prediction function may be to identify variables that predict the incidence of hip fractures. Such variables might, for example, include the use of some drugs the predispose patients to losing balance and falling, a history of falls, a diagnosis of osteoporosis, etc. This prediction may then be used to select from available interventions for preventing or reducing the incidence of hip fractures, such as, for example, a comprehensive medication review by a pharmacist, a home visit by a nurse, or prescribing of protective pads, etc.

While the foregoing system and method for health care management has been described in conjunction with illustrative non-limiting exemplary embodiments set forth herein, it will be understood that various changes may be made without departing from the true spirit and full scope of the invention as defined in the appended claims.

What is claimed is:

1. A method implemented using an information processing system having processing circuitry including, at least, a memory, a processor, a communications interface, and an input/output interface, the method comprising:
   using the processing circuitry of the information processing system:
      receiving, via the communications interface, communicating with at least one other information processing system, historical patient data for a population of patients;
      converting the historical patient data into patient-level data files;
      generating, using at least the patient-level data files, one or more setup variables by defining at least one time period, at least one dependent variable, and at least one independent variable;
      creating a resultant data file including the one or more setup variables, the resultant data file including, at least, training data and validation data;
      applying statistical methods to the training data and combining the statistical methods to generate ensemble methods;
      generating a prediction function using the training data in combination with the ensemble methods;
      testing the prediction function against the validation data to generate a resultant prediction function;
      identifying one or more candidate patients from the population of patients;
      generating an adherence score for each candidate patient by applying the resultant prediction function for each candidate patient;
      determining one or more available adherence intervention recommendations for each candidate patient;
      mapping the adherence score to an adherence intervention recommendation, selected from the one or more available adherence intervention recommendations, using a clinical decision analysis program;
      applying one or more intervention rules to the adherence intervention recommendation;
      determining a goal parameter specified by an entity based on factors that include at least one of minimizing cost, maximizing benefits, or maximizing benefits gained under a specified budget;
      determining a subset of patients from the one or more candidate patients based on, in part, the determined goal parameter; and
      generating output data associated with the adherence intervention recommendation for each patient included in the subset of patients, wherein
   the application of the intervention rules and determination of the goal parameter is performed in a repeated recursive manner based on a selected time period.

2. The method of claim 1, further comprising:
   obtaining tracking information by tracking adherence to the medication of interest for each patient in the subset of patients.

3. The method of claim 2, further comprising:
   revising said prediction function based on said tracking information by re-applying the prediction function to said tracking information of each patient in the subset of patients and providing an updated adherence score for each patient in the subset of patients; and
   providing a revised adherence intervention recommendation for each patient in the subset of patients based at least on said updated adherence score.

4. The method of claim 2, wherein said tracking information is provided in a repeated recursive manner based on a selected time period.

5. The method of claim 2, further comprising:
   changing the adherence intervention recommendation based on said tracking information.

6. The method of claim 1, further comprising:
   obtaining tracking information by tracking adherence to the medication of interest and other medications for each patient in the subset of patients.

7. The method of claim 6, further comprising:
   revising said prediction function based on said tracking information by re-applying the prediction function to said tracking information of each patient in the subset of patients and providing an updated adherence score for each patient in the subset of patients; and
   providing a revised adherence intervention recommendation for each patient in the subset of patients based at least on said updated adherence score.

8. The method of claim 1, further comprising:
   tracking information on the performance of each intervention.

9. The method of claim 8, further comprising:
   revising said prediction function based on the tracking information on the performance of each intervention; and
   providing a revised adherence intervention recommendation based on said revised prediction function.

10. The method of claim 1, wherein said independent variable is based on at least one of an attribute of the patient, an attribute of a drug regimen and/or an attribute of a health care system.

11. The method of claim 1, wherein at least one independent variable is derived from said historical patient data.

12. The method of claim 1, wherein said adherence intervention recommendation includes recommending no action or intervention.

13. The method of claim 1, wherein the adherence intervention recommendation is further selected based on additional inputs including, at least, a return on investment.

14. The method of claim 1, wherein the adherence intervention recommendation is generated by an intervention engine that is a computer based application receiving inputs including the adherence score.

15. The method of claim 14, wherein the intervention engine receives additional inputs including, at least, a true positive rate, a true negative rate, a false positive rate, a false negative rate, adherence goals each patient, and/or cost per patient for each defined adherence program.

16. The method of claim 1, wherein a prediction engine generates the adherence score and the adherence score is input into a computer implemented decision analysis matrix along with information for each patient and available interventions for each patient to determine the adherence intervention recommendation.

17. The method of claim 1, wherein the historical data includes, at least, pharmacy claims data and/or medical claims data.

18. The method of claim 1, wherein the adherence score is specific to each patient and reflects a probability of each patient experiencing an outcome represented by the at least one dependent variable.

19. A method implemented using an information processing system having processing circuitry including, at least, a memory, a processor, a communications interface, and an input/output interface, the method comprising:
   using the processing circuitry of the information processing system:
      receiving, via the communications interface, communicating with at least one other information processing system, historical patient data for a population of patients;
      creating a resultant data file, that includes training data and validation data, using the historical patient data by converting the historical patient data into patient-level data files and generating setup variables using the patient-level data files;
      generating a prediction function by, at least, applying statistical methods to the training data and testing the prediction function against the validation data;
      identifying one or more candidate patients;
      generating an adherence score for each candidate patient by applying the generated prediction function for each candidate patient;
      determining one or more available adherence intervention recommendations for each candidate patient;
      mapping the adherence score to an adherence intervention recommendation, selected from the one or more available adherence intervention recommendations;
      applying one or more intervention rules to the adherence intervention recommendation;
      determining a goal parameter specified by an entity based on factors that include at least one of minimizing cost, maximizing benefits, or maximizing benefits gained under a specified budget;
      determining a subset of patients from the one or more candidate patients based on, in part, the determined goal parameter; and
      generating output data associated with the adherence intervention recommendation for each patient included in the subset of patients, wherein
   the application of the intervention rules and determination of the goal parameter is performed in a repeated recursive manner based on a selected time period.

20. The method of claim 19, further comprising providing an expected response to each adherence intervention recommendation.

21. The method of claim 19, further comprising:
   obtaining tracking information by tracking adherence to the medication of interest for each patient in the subset of patients.

22. The method of claim 21, further comprising:
   revising said prediction function based on said tracking information by re-applying the prediction function to said tracking information of each patient in the subset of patients and providing an updated adherence score for each patient in the subset of patients; and
   providing a revised adherence intervention recommendation for each patient in the subset of patients based at least on said updated adherence score.

23. The method of claim 21, wherein said tracking information is provided in a repeated recursive manner based on a selected time period.

24. The method of claim 19, further comprising:
   obtaining tracking information by tracking adherence to the medication of interest and other medications for each candidate.

25. The method of claim 24, further comprising:
   revising said prediction function based on said tracking information by re-applying the prediction function to said tracking information of each patient in the subset of patients and providing an updated adherence score for each patient in the subset of patients; and
   providing a revised adherence intervention recommendation for each patient in the subset of patients based at least on said updated adherence score.

26. The method of claim 19, further comprising:
   tracking information on the performance of each intervention in a population
   revising said prediction function based on the tracking information on the performance of each intervention; and
   providing a revised adherence intervention recommendation based on said revised prediction function.

27. The method of claim 19, further comprising:
   revising said prediction function based on updated patient information.

28. The method of claim 19, further comprising:
   revising said prediction function based on updated intervention information or data;
   tracking adherence to the medication of interest for each patient in the subset of patients to obtain tracking information;
   revising said prediction function based on said tracking information by re-applying the prediction function to said tracking information of each patient in the subset of patients and providing an updated adherence score for each patient in the subset of patients; and
   providing a revised adherence intervention recommendation for each patient in the subset of patients based at least on said updated adherence score.

29. The method of claim 19, further comprising:
   generating a report that provides the recommended adherence intervention recommendation for each candidate patient.

30. The method of claim 19, wherein said recommended intervention includes recommending no action or intervention.

31. A system comprising at least one processor, a memory, an input/output interface, and a communications interface, the system configured to:
   receive, via the communications interface, communicating with at least one other information processing system, historical patient data for a population of patients;
   create a resultant data file, that includes training data and validation data, using the historical patient data by converting the historical patient data into patient-level data files and generating setup variables using the patient-level data files;

generate a prediction function by, at least, applying statistical methods to the training data and testing the prediction function against the validation data;
identify one or more candidate patients;
generate an adherence score for each candidate patient by applying the generated prediction function for each candidate patient;
determine one or more available adherence intervention recommendations for each candidate patient;
map the adherence score to an adherence intervention recommendation, selected from the one or more available adherence intervention recommendations;
apply one or more intervention rules to the adherence intervention recommendation;
determine a goal parameter specified by an entity based on factors that include at least one of minimizing cost, maximizing benefits, or maximizing benefits gained under a specified budget;
determine a subset of patients from the one or more candidate patients based on, in part, the determined goal parameter; and
generate output data associated with the adherence intervention recommendation for each patient included in the subset of patients, wherein
the application of the intervention rules and determination of the goal parameter is performed in a repeated recursive manner based on a selected time period.

32. A non-transitory computer-readable storage medium having a program executable by a computer having at least one processor, a memory, an input/output interface, and a communications interface, the program when executed causing the computer to provide execution comprising:
receiving, via the communications interface, communicating with at least one other information processing system, historical patient data for a population of patients;
creating a resultant data file, that includes training data and validation data, using the historical patient data by converting the historical patient data into patient-level data files and generating setup variables using the patient-level data files;
generating a prediction function by, at least, applying statistical methods to the training data and testing the prediction function against the validation data;
identifying one or more candidate patients;
generating an adherence score for each candidate patient by applying the generated prediction function for each candidate patient;
determining one or more available adherence intervention recommendations for each candidate patient;
mapping the adherence score to an adherence intervention recommendation, selected from the one or more available adherence intervention recommendations, using a clinical decision analysis program;
applying one or more intervention rules to the adherence intervention recommendation;
determining a goal parameter specified by an entity based on factors that include at least one of minimizing cost, maximizing benefits, or maximizing benefits gained under a specified budget;
determining a subset of patients from the one or more candidate patients based on, in part, the determined goal parameter; and
generating output data associated with the adherence intervention recommendation for each patient included in the subset of patients, wherein
the application of the intervention rules and determination of the goal parameter is performed in a repeated recursive manner based on a selected time period.

33. A system comprising at least one processor, a memory, an input/output interface, and a communications interface, the system configured to:
receive, via the communications interface, communicating with at least one other information processing system, historical patient data for a population of patients;
convert the historical patient data into patient-level data files;
generate, using at least the patient-level data files, one or more setup variables by defining at least one time period, at least one dependent variable, and at least one independent variable;
create a resultant data file including the one or more setup variables, the resultant data file including, at least, training data and validation data;
apply statistical methods to the training data and generate a prediction function;
test the prediction function against the validation data to generate a resultant prediction function;
identify one or more candidate patients from the one or more patients;
generate an adherence score for each candidate patient by applying the resultant prediction function for each candidate patient;
determine one or more available adherence intervention recommendations for each candidate patient;
map the adherence score to an adherence intervention recommendation, selected from the one or more available adherence intervention recommendations, using a clinical decision analysis program;
apply one or more intervention rules to the adherence intervention recommendation;
determine a goal parameter specified by an entity based on factors that include at least one of minimizing cost, maximizing benefits, or maximizing benefits gained under a specified budget;
determine a subset of patients from the one or more candidate patients based on, in part, the determined goal parameter; and
generate an output associated with the adherence intervention recommendation for each patient included in the subset of patients, wherein
the application of the intervention rules and determination of the goal parameter is performed in a repeated recursive manner based on a selected time period.

34. A non-transitory computer-readable storage medium having a program executable by a computer having at least one processor, a memory, an input/output interface, and a communications interface, the program when executed causing the computer to provide execution comprising:
receiving, via the communications interface, communicating with at least one other information processing system, historical patient data for a population of patients;
converting the historical patient data into patient-level data files;
generating, using at least the patient-level data files, one or more setup variables by defining at least one time period, at least one dependent variable, and at least one independent variable;
creating a resultant data file including the one or more setup variables, the resultant data file including, at least, training data and validation data;

applying statistical methods to the training data and generate a prediction function;
testing the prediction function against the validation data to generate a resultant prediction function;
identifying one or more candidate patients from the one or more patients;
generating an adherence score for each candidate patient by applying the resultant prediction function for each candidate patient;
determining one or more available adherence intervention recommendations for each candidate patient;
mapping the adherence score to an adherence intervention recommendation, selected from the one or more available adherence intervention recommendations, using a clinical decision analysis program;
applying one or more intervention rules to the adherence intervention recommendation;
determining a goal parameter specified by an entity based on factors that include at least one of minimizing cost, maximizing benefits, or maximizing benefits gained under a specified budget;
determining a subset of patients from the one or more candidate patients based on, in part, the determined goal parameter; and
generating output data associated with the adherence intervention recommendation for each patient included in the subset of patients, wherein
the application of the intervention rules and determination of the goal parameter is performed in a repeated recursive manner based on a selected time period.

* * * * *